(12) United States Patent
Legrand et al.

(10) Patent No.: US 6,641,618 B1
(45) Date of Patent: Nov. 4, 2003

(54) READY-TO-USE AQUEOUS COMPOSITION FOR BLEACHING KERATIN FIBERS, COMPRISING A COMBINATION OF A WATER-SOLUBLE SOLVENT AND A NONIONIC AND/OR ANIONIC AMPHIPHILIC POLYMER COMPRISING AT LEAST ONE FATTY CHAIN

(75) Inventors: Frédéric Legrand, Boulogne Billancourt (FR); Jean Millequant, Saint Maur (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/493,243

(22) Filed: Jan. 28, 2000

(30) Foreign Application Priority Data

Jan. 29, 1999 (FR) .............................. 99 01055

(51) Int. Cl.⁷ .............................. D06L 3/00; D06L 3/06
(52) U.S. Cl. .................. 8/101; 8/109; 8/111; 424/70.1; 424/DIG. 3
(58) Field of Search ............................ 8/412, 408, 411, 8/101, 109, 111; 424/70.1, DIG. 3

(56) References Cited

U.S. PATENT DOCUMENTS

| | | | | |
|---|---|---|---|---|
| 2,528,378 A | 10/1950 | Mannheimer | ............ | 260/309.6 |
| 2,781,354 A | 2/1957 | Mannheimer | ............ | 260/309.6 |
| 2,961,347 A | 11/1960 | Floyd | | |
| 3,227,615 A | 1/1966 | Korden | ...................... | 167/87.1 |
| 3,589,578 A | 6/1971 | Kamphausen | ................ | 226/40 |
| 3,915,921 A | 10/1975 | Schlatzer, Jr. | ............... | 260/17.4 |
| 3,940,351 A | 2/1976 | Schlatzer, Jr. | ............... | 260/17.4 |
| 4,031,307 A | 6/1977 | DeMartino et al. | ......... | 536/114 |
| 4,131,576 A | 12/1978 | Iovine et al. | ............... | 260/17.4 |
| 4,390,689 A | 6/1983 | Jacquet et al. | ............... | 528/335 |
| 4,507,278 A | 3/1985 | DeMarco et al. | ............. | 424/62 |
| 4,509,949 A | 4/1985 | Huang et al. | ................ | 586/558 |
| 4,702,906 A | 10/1987 | Jacquet et al. | ................ | 424/70 |
| 4,719,282 A | 1/1988 | Nadolsky et al. | ............ | 528/310 |
| 4,927,627 A | 5/1990 | Schrader et al. | ............. | 424/62 |
| 5,100,658 A | 3/1992 | Bolich, Jr. et al. | ............. | 424/70 |
| 5,106,609 A | 4/1992 | Bolich, Jr. et al. | ............. | 424/70 |
| 5,376,146 A | 12/1994 | Casperson et al. | ............. | 8/408 |
| 5,478,562 A | 12/1995 | Cauwet et al. | ............... | 424/401 |
| 5,609,651 A | 3/1997 | Mager et al. | .................. | 8/435 |
| 5,735,908 A | 4/1998 | Cotteret et al. | ................ | 8/410 |
| 5,976,195 A * | 11/1999 | de la Mettrie et al. | ......... | 8/411 |
| 5,989,295 A | 11/1999 | de la Mettrie et al. | ......... | 8/406 |
| 6,010,541 A * | 1/2000 | de la Mettrie et al. | ......... | 8/412 |
| 6,312,677 B1 | 11/2001 | Millequant et al. | ...... | 424/70.17 |

FOREIGN PATENT DOCUMENTS

| | | |
|---|---|---|
| EP | 0 080 976 | 6/1983 |
| EP | 0 216 479 | 4/1987 |
| EP | 0 241 707 | 10/1987 |
| EP | 0 337 354 | 10/1989 |
| EP | 0 557 203 | 8/1993 |
| EP | 0 664 114 | 7/1995 |
| EP | 0 825 200 | 2/1998 |
| EP | 0 827 738 | 3/1998 |
| EP | 0 875 237 | 11/1998 |
| EP | 0 882 444 | 12/1998 |
| FR | 1 400 366 | 4/1965 |
| FR | 1 492 597 | 8/1967 |
| FR | 1 583 363 | 9/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 368 508 | 5/1978 |
| FR | 2 383 660 | 10/1978 |
| FR | 2 393 573 | 1/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| GB | 2 192 645 | 1/1988 |
| WO | WO 91/11985 | 8/1991 |
| WO | WO 97/07776 | 3/1997 |
| WO | WO 97/24105 | 7/1997 |
| WO | WO 97/24106 | 7/1997 |
| WO | WO 97/24107 | 7/1997 |
| WO | WO 98/03150 | 1/1998 |

OTHER PUBLICATIONS

M.R. Porter, "Handbook of Surfactants", Blackie & Son Ltd. (Glasgow and London), 1991, pp. 116–178.
English language Derwent Abstract of EP 0 080 976, Jun. 8, 1983.
English language Derwent Abstract of EP 0 557 203, Aug. 29, 1993.
English language Derwent Abstract of FR 1 583 363, Sep. 15, 1969.
English language Derwent Abstract of FR 2 077 143, Oct. 15, 1971.
English language Derwent Abstract of FR 2 080 759. Nov. 19, 1971.
English language abstract of FR 2 162 025. Jul. 13, 1973.
English language Derwent Abstract of FR 2 190 406. Feb. 1, 1974.
English language Derwent Abstract of FR 2 252 840. Jun. 27, 1975.
English language Derwent Abstract of FR 2 270 846. Dec. 12, 1975.

(List continued on next page.)

Primary Examiner—Lorna M. Douyon
Assistant Examiner—Eisa Elhilo
(74) Attorney, Agent, or Firm—Finnegan, Henderson, Farabow, Garrett & Dunner, L.L.P.

(57) ABSTRACT

Ready-to-use aqueous composition for bleaching keratin fibers, in particular, human keratin fibers, containing a combination of at least one alkaline agent, at least one peroxygenated salt, hydrogen peroxide, at least one water-soluble solvent, and at least one amphiphilic polymer chosen from nonionic and anionic amphiphilic polymers and comprising at least one fatty chain, and a process for bleaching the hair using these aqueous compositions.

42 Claims, No Drawings

OTHER PUBLICATIONS

English language Derwent Abstract of FR 2 280 361. Feb. 27, 1978.
English language abstract of FR 2 368 508. May 19, 1978.
English language Derwent Abstract of FR 2 383 660. Oct. 13, 1975.
English language abstract of FR 2 393 573. Jan. 5, 1979.
English language abstract of FR 2 470 596. Jun. 12, 1981.
English language abstract of FR 2 505 348. Nov. 12, 1982.
English language abstract of FR 2 519 863. Jul. 22, 1983.
English language abstract of FR 2 542 997. Sep. 28, 1984.
English language Derwent Abstract of FR 2 598 611. Nov. 20, 1987.
English language Derwent Abstract of EP 0 882 444. Dec. 9, 1998.
Aculyn 44 Cosmetic Grade, 1996 Rohm & Haas Co., pp. 1–8.
Aculyn 46 Cosmetic Grade, 1997 Rohm & Haas Co., pp. 1–8.
Rheology Modifiers for Personal Care Applications, 1994 Rohm & Haas Co., p. 1.
Thickener applications, Aculyn 22, 33 et 44, 1994 Rhom & Haas Co., p. 1.
Aculyn 44 Cosmetic Grade, 1994 Rhom & Haas Co., pp. 1–8.
Aculyn Thickeners and Stabilizers, 1994 Rohm & Haas Co., pp. 1–8.
Aculyn Thickeners and Stabilizers, 1996 Rohm & Haas Co., pp. 1–8.
Karlheinz Schrader, "Grundlagen und Rezepturen der Kosmetika," 1989, pp. 1–17.
Jones, Charles E., Ph.D., "Polymers in Cosmetics," 1993, pp. 1–10.
Pollena TSPK, Rohm & Haas Symposium, No. 10, 1993, vol. 37, pp. 1–13.
Julie Schumucker–Castner & Dilip Desai, Rheology Modification of Hydrogen Peroxide–Based Applications Using Cross–Linked Polyacrylic Acid Polymers, 1997, pp. 1–11.
Charles Zviak, "The Science of Hair Care," 1986, pp. 1–25.

* cited by examiner

READY-TO-USE AQUEOUS COMPOSITION FOR BLEACHING KERATIN FIBERS, COMPRISING A COMBINATION OF A WATER-SOLUBLE SOLVENT AND A NONIONIC AND/OR ANIONIC AMPHIPHILIC POLYMER COMPRISING AT LEAST ONE FATTY CHAIN

The present invention relates to ready-to-use aqueous compositions for bleaching keratin fibers, comprising a combination of at least one water-soluble solvent and at least one nonionic and/or anionic amphiphilic polymer comprising at least one fatty chain, to a process for bleaching keratin fibers using these compositions, and to a packaging kit containing such a composition.

To bleach hair, it is possible to use aqueous compositions resulting from the mixing, at the time of application, of an aqueous hydrogen peroxide composition, an aqueous composition containing an alkaline agent and at least one water-soluble solvent and a powder containing a peroxygenated reagent such as ammonium or alkali metal persulphates, perborates or percarbonates.

In the field of hair bleaching, bleaching compositions are generally sought that are thick enough to allow a precise application onto certain regions of the head of hair, and that do not run the risk of running onto the face or beyond the regions to be bleached.

The thickening or gelling effect is conventionally obtained with traditional thickeners such as cellulose derivatives, starch derivatives, alginates, thickening silicates or mixtures of carefully selected surfactants. However, when these traditional thickeners are used, there is a large decrease in the viscosity of the final bleaching composition over time.

There is thus a need for a thickening system capable of maintaining a high viscosity for the time required to obtain the desired bleaching effect, generally between ten minutes and one hour.

The inventors have discovered, surprisingly, that it is possible to improve, considerably, the maintenance of the viscosity over time of the bleaching compositions described above by combining the initial system with a nonionic and/or anionic amphiphilic polymer comprising at least one fatty chain.

They have also found that this thickening system allows much larger dilutions with aqueous hydrogen peroxide compositions than the known thickening systems.

One subject of the present invention is consequently a ready-to-use aqueous composition for bleaching keratin fibers, especially human keratin fibers, comprising, in a medium suitable for bleaching, at least one alkaline agent, at least one water-soluble solvent, hydrogen peroxide, at least one peroxygenated salt and, in addition, at least one nonionic and/or anionic amphiphilic polymer comprising at least one fatty chain.

A further subject of the invention is a process for bleaching keratin fibers using the aqueous bleaching composition described above, as well as a packaging kit containing such a composition.

Other subjects, features and advantages of the invention will become apparent on reading the written description, the examples and the claims which follow, or may be learned upon practice of the invention. Both the foregoing general description and the following detailed description of the invention are exemplary and explanatory only and are not restrictive of the claimed invention.

The nonionic amphiphilic polymers comprising at least one fatty chain which can be used according to the present invention encompass, for example:

celluloses or hydroxyalkylcelluloses modified with groups comprising at least one fatty chain, such as an alkyl, arylalkyl or alkylaryl group containing an alkyl group which is preferably $C_8$–$C_{22}$, such as the products NATROSOL PLUS GRADE 330 CS from the company Aqualon, BERMOCOLL EHM 100 from the company Berol Nobel, or POLYSURF 67 from the company Hercules, or modified with polyalkoxylated alkylphenol groups, such as the product AMERCELL POLYMER HM-1500 from the company Amerchol;

hydroxypropyl guars modified with groups comprising at least one $C_8$–$C_{22}$ fatty chain such as the products ESAFLOR HM 22 ($C_{22}$ alkyl chain) from the company Lamberti, or MIRACARE XC95-3 ($C_{14}$ alkyl chain) and RE205-1 ($C_{20}$ alkyl chain) from the company Rhone-Poulenc;

polyurethanes comprising at least one fatty chain of $C_8$–$C_{30}$ alkyl or alkenyl type such as SER-AD FX 1100 from the company Servo Delben;

the SMDI (saturated methylene diphenyl diisocyanate) polyethylene glycol(s) copolymer with a decyl end group;

the SMDI (saturated methylene diphenyl diisocyanate) polyethylene glycol(s) copolymer with an alkyl (methyl/$C_{18}$) end group, combined with a maltodextrin matrix;

the HMDI (hexamethylene diisocyanate) diurethane of oxyethylenated (66 EO) and oxypropylenated (14 PO) $C_{10}$–$C_{18}$ alcohols, sold under the name ELFACOS T 212 by the company Akzo;

copolymers of vinylpyrrolidone and of hydrophobic monomers containing a fatty chain, such as the products ANTARON V216 or GANEX V216 (poly(vinylpyrrolidone/hexadecene)), ANTARON V220 or GANEX V220 (poly(vinylpyrrolidone/eicosene)) from the company ISP;

copolymers of $C_1$–$C_6$ alkyl (meth)acrylates and of amphiphilic monomers comprising at least one fatty chain;

copolymers of hydrophilic (meth)acrylates and of hydrophobic monomers comprising at least one fatty chain, for example a poly(polyethylene glycol methacrylate/lauryl methacrylate).

Polyurethanes comprising at least one $C_{10}$–$C_{20}$ alkyl fatty chain and hydroxyethylcelluloses modified with groups comprising at least one $C_8$–$C_{22}$ alkyl radical are particularly preferred.

The anionic amphiphilic polymers comprising at least one fatty chain used according to the present invention are crosslinked or non-crosslinked copolymers comprising hydrophilic units derived from one or more monomers containing ethylenic unsaturation bearing a free carboxylic acid function, and hydrophobic units derived from one or more monomers containing ethylenic unsaturation bearing a hydrophobic side chain, and optionally crosslinking units derived from one or more polyunsaturated monomers.

The monomer(s) containing ethylenic unsaturation bearing a carboxylic acid function is(are) chosen from ethacrylic acid, methacrylic acid and acrylic acid, preferably from methacrylic acid and acrylic acid and mixtures thereof.

The monomer(s) containing ethylenic unsaturation bearing a hydrophobic side chain can be (i) fatty alkyl esters of unsaturated carboxylic acids, or (ii) allyl fatty alkyl ethers.

(i) The fatty alkyl esters of unsaturated carboxylic acids are chosen, for example, from $C_{10}$–$C_{30}$, preferably $C_{12}$–$C_{22}$, alkyl ethacrylates, methacrylates and/or acrylates.

They encompass, for example, lauryl acrylate, stearyl acrylate, decyl acrylate, isodecyl acrylate and dodecyl acrylate, as well as the corresponding methacrylates, i.e., lauryl methacrylate, stearyl methacrylate, decyl methacrylate, isodecyl methacrylate and dodecyl methacrylate.

(ii) The allyl fatty alkyl ethers forming the hydrophobic units of the anionic amphiphilic polymers of the present invention correspond to the formula

$$CH_2=CR'CH_2-O-B_n-R \qquad (I)$$

in which $R^1$ is a hydrogen atom or a methyl group,

B is an ethylenoxy group, n is an integer ranging from 0 to 100,

R is a hydrocarbon-based group chosen from alkyl, arylalkyl, aryl, alkylaryl and cycloalkyl residues comprising from 8 to 30 carbon atoms, preferably from 10 to 24 carbon atoms, and more preferably from 12 to 18 carbon atoms.

One preferred unit of formula (I) according to the present invention is a unit in which $R^1$ represents a hydrogen atom, n is equal to 10 and R represents a stearyl ($C_{18}$) radical.

The crosslinking monomer is a compound comprising at least two non-conjugated polymerizable double bonds. Examples include diallyl phthalate, allyl (meth)acrylate, divinylbenzene, (poly)ethylene glycol dimethacrylate, methylenebisacrylamide, polyallylsucrose or polyallylpentaerythritol.

Anionic amphiphilic polymers of the type described above are described, for example, in U.S. Pat. Nos. 3,915,921 and 4,509,949 (copolymers of (eth/meth)acrylic acid and of $C_{10}$–$C_{30}$ alkyl (eth/meth)acrylates), or in European patent EP-0 216 479 B2 (copolymers of (eth/meth)acrylic acid and of allyl fatty alcohol ethers), the disclosures of all of which are hereby incorporated by reference.

Examples of preferred polymers include:

crosslinked polymers of acrylic acid and of $C_{10}$–$C_{30}$ alkyl acrylate, such as the polymers sold under the names PEMULEN TR1, PEMULEN TR2 and CARBOPOL 1382 by the company Goodrich, the crosslinked polymer of acrylic acid and of $C_{10}$–$C_{30}$ alkyl methacrylate, such as CARBOPOL ETD 2020 sold by the company Goodrich, the oxyethylenated methacrylic acid/ethyl acrylate/stearyl methacrylate (55/35/10) terpolymer, the oxyethylenated (25 EO) (meth)acrylic acid/ethyl acrylate/behenyl methacrylate terpolymer, and the crosslinked methacrylic acid/ethyl acrylate/steareth-10 allyl ether terpolymer.

These nonionic and/or anionic amphiphilic polymers comprising at least one fatty chain are used in a proportion of from 0.01 to 10% by weight, preferably in a proportion of 0.1 to 5% by weight, relative to the aqueous bleaching composition.

As indicated above, the aqueous bleaching composition also contains at least one alkaline agent, at least one peroxygenated salt, at least one water-soluble solvent and hydrogen peroxide.

The alkaline agent is chosen from aqueous ammonia and organic amines such as monoethanolamine, diethanolamine, triethanolamine, 2-amino-2-methyl-1-propanol, diaminopropane, hydroxyalkylamines and ethylenediamines which are oxyethylenated and/or oxypropylenated.

The peroxygenated salts are chosen from the ammonium or alkali metal persulphates, percarbonates and perborates. Persulphates are preferably used, and among these sodium persulphate and potassium persulphate are mainly used. The compositions of the invention contain from 2% to 20% by weight and preferably from 4 to 15% by weight of peroxygenated salt, relative to the total weight of the composition.

For the purposes of the present invention, the expression "water-soluble solvents" means solvents which are soluble to more than 5% by weight in water at 250° C. The water-soluble solvents of the invention are preferably chosen from linear or branched $C_{1-6}$ aliphatic monoalcohols, linear or branched $C_{3-20}$ aliphatic polyols, polyol ethers including aliphatic $C_{1-6}$ mono- or diethers of $C_{2-9}$ polyols and $C_{6-9}$ aromatic ethers of $C_{2-9}$ polyols. The compositions of the invention contain from 0.1 to 10% by weight, preferably from 0.5 to 8% by weight, of water-soluble solvent, relative to the total weight of the composition. They also contain from 0.5 to 10% by weight, preferably from 1 to 8% by weight, of hydrogen peroxide, relative to the total weight of the composition.

The aqueous bleaching compositions of the present invention can also contain bleaching adjuvants of any kind capable of facilitating the handling and application, of improving the storage and efficacy of the compositions and of improving the cosmetic properties of the treated hair. These adjuvants are, for example, agents for controlling the release of oxygen, such as magnesium carbonate and magnesia, anionic, nonionic, cationic, amphoteric or zwitterionic surfactants and mixtures thereof, mineral or plant oils, waxes, binders, mineral fillers such as silica and clay, opacifiers such as titanium oxide, dyes, sequestering agents, fragrances and polymers.

The compositions of the invention can, in particular, contain at least one natural or synthetic thickening water-soluble polymer and/or at least one cationic and/or amphoteric substantive polymer.

Needless to say, a person skilled in the art will take care to select this or these optional additional compounds and the amount thereof such that the advantageous properties intrinsically associated with the bleaching composition according to the invention are not, or are not substantially, adversely affected by the addition(s) envisaged.

The compositions of the invention preferably comprise at least one surfactant. The surfactants suitable for carrying out the present invention are, in particular, the following:

(i) Anionic surfactant(s):

As examples of anionic surfactants which can be used, alone or as mixtures, in the context of the present invention, examples include, in particular, salts (in particular, alkali metal salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates and ($C_6$–$C_{24}$)acyl glutamates. It is also possible to use ($C_6$–$C_{24}$) alkylpolyglycoside carboxylic esters such as alkylglucoside citrates, alkylpolyglycoside tartrate and alkylpolyglycoside sulphosuccinates, alkyl sulphosuccinamates; acyl isethionates and N-acyltaurates, the alkyl or acyl radical of all these various compounds preferably comprising from 12 to 20 carbon atoms, and the aryl radical preferably denoting a phenyl or benzyl group. Among the anionic surfactants which can also be used, examples include fatty acid salts such as oleic, ricinoleic, palmitic and stearic acid salts, coconut oil acid or hydrogenated coconut oil acid; acyl lactylates in which the acyl radical comprises 8 to 20 carbon atoms. Alkyl D-galactosiduronic acids and salts thereof, polyoxyalkylenated ($C_6$–$C_{24}$)alkyl ether carboxylic acids, polyoxyalkylenated ($C_6$–$C_{24}$)alkylaryl ether carboxylic acids and polyoxyalkylenated ($C_6$–$C_{24}$)alkylamido ether carboxylic acids and salts thereof, especially those comprising from 2 to 50 alkylene oxide groups, in particular, ethylene oxide groups and mixtures thereof, can also be used.

(ii) Nonionic surfactant(s):

The nonionic surfactants are, themselves also, compounds that are well known per se (see, in particular, in this respect "Handbook of Surfactants" by M. R. Porter, published by Blackie & Son (Glasgow and London), 1991, pp. 116–178) and, in the context of the present invention, their nature is not a critical feature. Thus, they can be chosen, in particular, from polyethoxylated or polypropoxylated fatty acids, alkylphenols, α-diols or alcohols having a fatty chain containing, for example, 8 to 18 carbon atoms, it being possible for the number of ethylene oxide or propylene oxide groups to range, in particular, from 2 to 50. Examples include copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and, in particular, 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or zwitterionic surfactant(s):

The amphoteric or zwitterionic surfactants, whose nature is not a critical feature in the context of the present invention, can be, in particular, aliphatic secondary or tertiary amine derivatives in which the aliphatic radical is a linear or branched chain containing 8 to 18 carbon atoms and containing at least one water-soluble anionic group (for example carboxylate, sulphonate, sulphate, phosphate or phosphonate); mention may also be made of ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido-($C_1$–$C_6$) alkylsulphobetaines.

Among the amine derivatives, examples include the products described in U.S. Pat. Nos. 2,528,378 and 2,781,354, the disclosures of which are hereby incorporated by reference, and classified in the CTFA dictionary, $3^{rd}$ edition, 1982, under the names Amphocarboxyglycinates and Amphocarboxypropioniates, and having the respective structures:

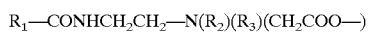

in which:

R$_1$ is an alkyl radical derived from an acid R$_1$—COOH present in hydrolyzed coconut oil, or R$_1$ is a heptyl, nonyl or undecyl radical, R$_2$ is a β-hydroxyethyl group and R$_3$ is a carboxymethyl group; and

in which:

B is —CH$_2$CH$_2$OX',

C is —(CH$_2$)$_z$—Y', with z=1 or 2,

X' is the —CH$_2$CH$_2$—COOH group or a hydrogen atom,

Y' is —COOH or the —CH$_2$—CHOH—SO$_3$H radical,

R$_{1'}$ is an alkyl radical of an acid R$_{1'}$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid.

(iv) Cationic surfactants:

Among the cationic surfactants which may be mentioned, in particular, are: optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can represent from 0.01 to 40%, and preferably from 0.1 to 30%, of the total weight of the composition.

The cationic substantive polymers which can be used in accordance with the present invention can be chosen from any of those already known per se as improving the cosmetic properties of the hair, in particular, those described in European patent applications EP-A-337354 and EP-A-557203 and in French patents FR-2,270,846; 2,383,660; 2,598,611; 2,470,596 and 2,519,863, the disclosures of which are hereby incorporated by reference.

The preferred cationic polymers are chosen from those which contain units comprising primary, secondary, tertiary and/or quaternary amine groups which can either form part of the main polymer chain or can be borne by a side substituent directly linked thereto.

The cationic polymers used generally have a number-average molecular mass of from 500 to $5 \times 10^6$ approximately, and preferably from $10^3$ to $3 \times 10^6$ approximately.

Among the cationic polymers which can be mentioned more particularly are polymers such as polyamine, polyamino amide and polyquaternary ammonium.

These are known products. They are described, in particular, in French patent Nos. 2,505,348 or 2,542,997, the disclosures of which are hereby incorporated by reference. Among the polymers which may be mentioned are:

(1) homopolymers or copolymers derived from acrylic or methacrylic esters or amides and comprising at least one of the units of formula (II), (III), (IV) or (V) below:

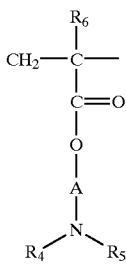
(II)

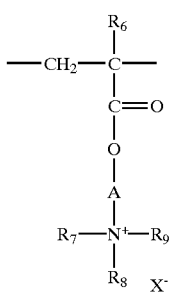
(III)

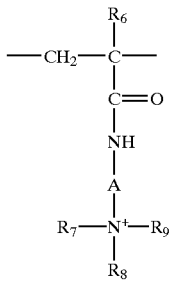
(IV)

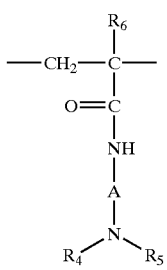
(V)

in which:
$R_6$, which may be identical or different, is a hydrogen atom or a $CH_3$ radical;
A, which may be identical or different, is a linear or branched alkyl group of 1 to 6 carbon atoms, preferably 2 or 3 carbon atoms, or a hydroxyalkyl group of 1 to 4 carbon atoms;
$R_7$, $R_8$ and $R_9$, which may be identical or different, are chosen from an alkyl group containing from 1 to 18 carbon atoms and a benzyl radical, and preferably an alkyl group containing from 1 to 6 carbon atoms;

$R_4$ and $R_5$, which may be identical or different, are chosen from hydrogen and an alkyl group containing from 1 to 6 carbon atoms, and preferably methyl or ethyl;
X is an anion derived from an inorganic or organic acid, such as a methosulphate anion or a halide such as chloride or bromide.

The polymers of the family (1) can also contain one or more units derived from comonomers which can be chosen from the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyllactams such as vinylpyrrolidone or vinylcaprolactam, and vinyl esters.

Thus, among these polymers of family (1) which may be mentioned are:
copolymers of acrylamide and of dimethylaminoethyl methacrylate quaternized with dimethyl sulphate or with a dimethyl halide,
copolymers of acrylamide and of methacryloyloxyethyl-trimethylammonium chloride described, for example, in European patent application EP-A-080976, the disclosure of which is hereby incorporated by reference,
the copolymer of acrylamide and of methacryloyloxyethyltrimethylammonium methosulphate,
quaternized or non-quaternized vinylpyrrolidone/ dialkylaminoalkyl acrylate or methacrylate copolymers. These polymers are described in detail in French patents 2,077,143 and 2,393,573, the disclosures of which are hereby incorporated by reference,
dimethylaminoethyl methacrylate/vinylcaprolactam/ vinylpyrrolidone terpolymers,
vinylpyrrolidone/methacrylamidopropyidimethylamine copolymers, and
quaternized vinylpyrrolidone/ dimethylaminopropylmethacrylamide copolymers.

(2) Other polymers include the cellulose ether derivatives containing quaternary ammonium groups, described in French patent 1,492,597, the disclosure of which is hereby incorporated by reference. These polymers are also defined in the CTFA dictionary as quaternary ammoniums of hydroxyethylcellulose which has reacted with an epoxide substituted with a trimethylammonium group.

(3) Cationic cellulose derivatives such as cellulosecopolymers or cellulose derivatives grafted with a water-soluble monomer of quaternary ammonium, and described in particular in U.S. Pat. No. 4,131,576, the disclosure of which is hereby incorporated by reference, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

(4) The cationic polysaccharides described, more particularly, in U.S. Pat. Nos. 3,589,578 and 4,031,307, the disclosures of which are hereby incorporated by reference, such as guar gums containing cationic trialkylammonium groups. Guar gums modified with a salt (e.g., chloride) of 2,3-epoxypropyltrimethylammonium are used, for example.

(5) Polymers comprising piperazinyl units and divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361, the disclosures of which are hereby incorporated by reference.

(6) Water-soluble polyamino amides prepared, in particular, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2,252,840 and 2,368,508, the disclosures of which are hereby incorporated by reference.

(7) The polyamino amide derivatives resulting from the condensation of polyalkylene polyamines with polycarboxylic acids followed by alkylation with difunctional agents. Examples include adipic acid/dialkylaminohydroxyalkyl-dialkylenetriamine polymers in which the alkyl radical contains from 1 to 4 carbon atoms and preferably denotes methyl, ethyl or propyl. Such polymers are described in particular in French patent 1,583,363, the disclosure of which is hereby incorporated by reference.

Among these derivatives, particular examples include the adipic acid/dimethylaminohydroxypropyl/diethylenetriamine polymers sold under the name CARTARETINE F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described, in particular, in U.S. Pat. Nos. 3,227,615 and 2,961,347, the disclosures of which are hereby incorporated by reference.

(9) Cyclopolymers of alkyldiallylamine or of dialkyldiallylammonium, such as the homopolymers or copolymers containing, as main constituent of the chain, units corresponding to formula (VI) or (VII):

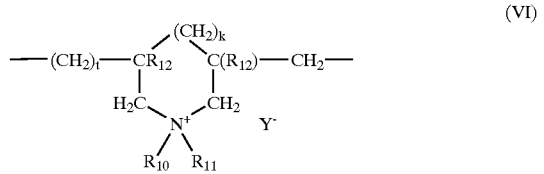

(VI)

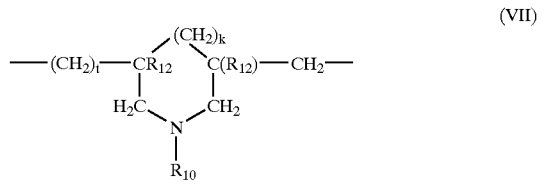

(VII)

in which formulae k and t are equal to 0 or 1, the sum k+t being equal to 1; $R_{12}$ is chosen from a hydrogen atom and a methyl radical; $R_{10}$ and $R_{11}$, independently of each other, are chosen from an alkyl group having from 1 to 22 carbon atoms, a hydroxyalkyl group in which the alkyl group preferably has 1 to 5 carbon atoms, and a lower ($C_1$–$C_4$) amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described, in particular, in French patent 2,080,759 and in its Certificate of Addition 2,190,406, the disclosures of which are hereby incorporated by reference.

(10) The quaternary diammonium polymer containing repeating units corresponding to the formula:

(VIII)

in which $R_{13}$, $R_{14}$, $R_{15}$ and $R_{16}$, which may be identical or different, are chosen from aliphatic, alicyclic or arylaliphatic radicals containing from 1 to 20 carbon atoms and lower hydroxyalkylaliphatic radicals, or, alternatively, $R_{13}$, $R_{14}$, $R_{15}$ and $R_{16}$, together or separately, constitute, with the nitrogen atoms to which they are attached, heterocycles optionally containing a second heteroatom other than nitrogen, or, alternatively, $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;

$A_1$ and $B_1$ are chosen from polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ is an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO—D—OC—$(CH_2)_n$— in which D denotes:

a) a glycol residue of formula:
—O—Z—O—, where Z denotes a linear or branched hydrocarbon radical or a group corresponding to one of the following formulae:

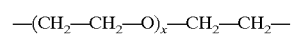

and

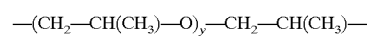

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or, alternatively, the divalent radical

—CH₂—CH₂—S—S—CH₂—CH₂—;

d) a ureylene group of formula: —NH—CO—NH—.

Preferably, X is an anion such as chloride or bromide.

These polymers generally have a number-average molecular mass of between 1000 and 100,000.

Polymers of this type are described in particular in French patents 2,320,330; 2,270,846; 2,316,271; 2,336,434 and 2,413,907 and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945 and 4,027,020, the disclosures of which are hereby incorporated by reference.

Polymers which can be used more particularly are those comprising repeating units corresponding to formula (IX) below:

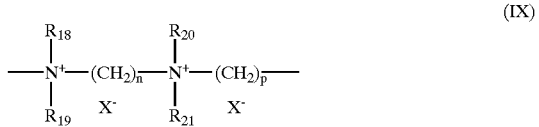

(IX)

in which $R_{18}$, $R_{19}$, $R_{20}$ and $R_{21}$, which may be identical or different, denote an alkyl or hydroxyalkyl radical containing from 1 to 4 carbon atoms approximately, n and p are integers ranging from 2 to 20 approximately and $X^-$ is an anion derived from an inorganic or organic acid.

(11) Polyquaternary ammonium polymers comprising units of formula (X):

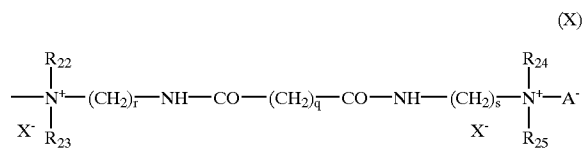

(X)

in which formula:

$R_{22}$, $R_{23}$, $R_{24}$ and $R_{25}$, which may be identical or different, are chosen from hydrogen and methyl, ethyl, propyl, b-hydroxyethyl, β-hydroxypropyl and —CH₂CH₂(OCH₂CH₂)$_p$OH radicals, where p is equal to 0 or to an integer ranging from 1 to 6, with the proviso that $R_{22}$, $R_{23}$, $R_{24}$ and $R_{25}$ do not simultaneously represent a hydrogen atom, r and s, which may be identical or different, are integers ranging from 1 to 6, q is equal to 0 or to an integer from 1 to 34, X is a halogen atom, A is a dihalide radical or preferably represents —CH₂—CH₂—O—CH₂—CH₂—.

Such compounds are described, in particular, in European patent application EP-A-122,324, the disclosure of which is hereby incorporated by reference.

(12) Quaternary polymers of vinylpyrrolidone and of vinylimidazole.

(13) Polyamines such as the product referred to under the name Polyethylene glycol (15) tallow polyamine in the CTFA dictionary.

(14) Crosslinked polymers of methacryloyloxy ($C_1$–$C_4$) alkyltri($C_1$–$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing olefinic unsaturation, in particular, methylenebisacrylamide. It is more particularly possible to use an acrylamide/methacryloyloxyethyltrimethylammonium chloride (20/80 by weight) crosslinked copolymer in the form of a dispersion containing 50% by weight of the copolymer in mineral oil. This dispersion is sold under the name "Salcare® SC 92" by the company Allied Colloids. It is also possible to use a crosslinked homopolymer of methacryloyloxyethyltrimethylammonium chloride containing about 50% by weight of the homopolymer in mineral oil or in a liquid ester. These dispersions are sold under the names Salcare® SC 95 and Salcare® SC 96 by the company Allied Colloids.

Other cationic substantive polymers which can be used in the context of the invention are polyalkyleneimines, in particular, polyethyleneimines, polymers containing vinylpyridine or vinylpyridinium units, condensates of polyamines and epichlorohydrin, polyquaternary ureylenes and chitin derivatives.

The amphoteric substantive polymers which can be used according to the present invention can be chosen from polymers containing units K and M distributed randomly in the polymer chain, in which K denotes a unit derived from a monomer containing at least one basic nitrogen atom and M denotes a unit derived from an acid monomer containing one or more carboxylic or sulphonic groups, or, alternatively, K and M can denote groups derived from carboxybetaine or sulphobetaine zwitterionic monomers;

K and M can also denote a cationic polymer chain containing primary, secondary, tertiary or quaternary amine groups, in which at least one of the amine groups bears a carboxylic or sulphonic group connected via a hydrocarbon radical or, alternatively, K and M form part of a chain of a polymer containing an α, β-dicarboxylic ethylene unit in which one of the carboxylic groups has been made to react with a polyamine containing one or more primary or secondary amine groups.

The preferred amphoteric film-forming polymers corresponding to the definition given above are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537, the disclosure of which is hereby incorporated by reference. Examples also include sodium acrylate/acrylamidopropyltrimethylammonium chloride copolymer. The vinyl compound can also be a dialkyldiallylammonium salt such as diethyl-diallylammonium chloride.

(2) polymers containing units derived from:

a) at least one monomer chosen from acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides. The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides. The preferred basic comonomers are aminoethyl, butylaminoethyl, N,N'-dimethylaminoethyl and N-tert-butylaminoethyl methacrylates. The copolymers whose CTFA (4th edition, 1991) name is octylacrylamide/acrylates/butylaminoethyl methacrylate copolymer are particularly used.

(3) crosslinked and alkylated polyamino amides partially or totally derived from polyamino amides of formula:

(XI)

in which $R_{26}$ is a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the acids to a bis(primary) or bis(secondary) amine, and Z denotes a bis(primary); mono- or bis(secondary) polyalkylene-polyamine radical and preferably represents:

a) in proportions of from 60 to 100 mol %, the radical

(XII)

where x=2 and p=2 or 3, or alternatively x=3 and p=2, this radical being derived from diethylenetriamine, from triethylenetetraamine or from dipropylenetriamine;

b) in proportions of from 0 to 40 mol %, the radical (XII) above in which x=2 and p=1 and which is derived from ethylenediamine, or the radical derived from piperazine:

c) in proportions of from 0 to 20 mol %, the —NH—(CH$_2$)$_6$—NH— radical derived from hexamethylenediamine, these polyamino amines being crosslinked by addition of a difunctional crosslinking agent chosen from epihalohydrines, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid. The alkane sultones used in the alkylation are preferably propane sultone or butane sultone, the salts of the alkylating agents are preferably the sodium or potassium salts.

(4) polymers containing zwitterionic units of formula:

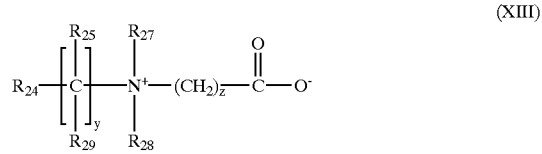

(XIII)

in which $R_{27}$ is a polymerizable unsaturated group such as an acrylate, methacrylate, acrylamide or methacrylamide group, y and z represent an integer from 1 to 3, $R_{28}$ and $R_{29}$ is chosen from hydrogen and methyl, ethyl and propyl radicals, $R_{30}$ and $R_{31}$ are chosen from a hydrogen atom and an alkyl radical such that the sum of the carbon atoms in $R_{30}$ and $R_{31}$ does not exceed 10.

The polymers comprising such units can also contain units derived from non-zwitterionic monomers such as dimethyl- or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethyl methacryate.

(5) polymers derived from chitosan containing monomer units corresponding to formulae (XIV), (XV) and (XVI) below:

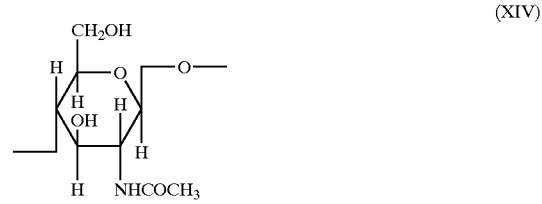

(XIV)

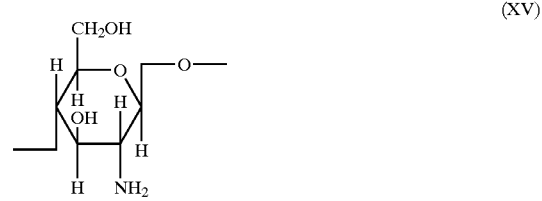

(XV)

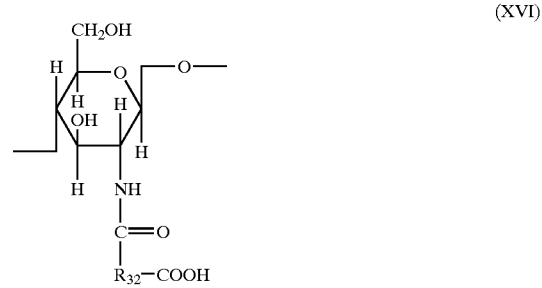

(XVI)

the unit XIV being present in proportions ranging from 0 to 30%, the unit XV in proportions ranging from 5 to 50% and the unit XVI in proportions ranging from 30 to 90%, it being understood that, in this unit F, $R_{32}$ represents a radical of formula:

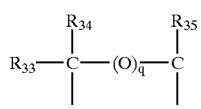 (XVII)

in which if q=0, $R_{33}$, $R_{34}$ and $R_{35}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, or an alkylthio residue in which the alkyl group bears an amino residue, at least one of the radicals $R_{33}$, $R_{34}$ and $R_{35}$ being, in this case, a hydrogen atom;

or, if q=1, $R_{33}$, $R_{34}$ and $R_{35}$ each represent a hydrogen atom, as well as the salts formed by these compounds with bases or acids.

(6) polymers derived from the N-carboxyalkylation of chitosan, such as N-carboxymethylchitosan or N-carboxybutylchitosan.

(7) polymers corresponding to the general formula (XVIII) as are described, for example, in French patent 1,400,366, the disclosure of which is hereby incorporated by reference:

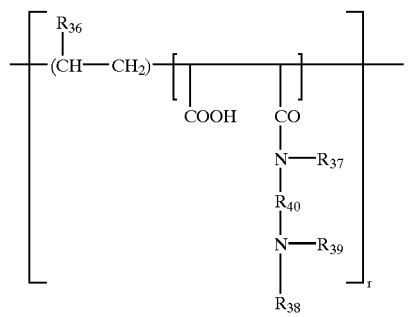 (XVIII)

in which $R_{36}$ is chosen from represents a hydrogen atom, a $CH_3O$, $CH_3CH_2O$ or phenyl radical, $R_{37}$ denotes hydrogen or a lower alkyl radical such as methyl or ethyl, $R_{38}$ denotes hydrogen or a lower alkyl radical such as methyl or ethyl, $R_{39}$ denotes a lower alkyl radical such as methyl or ethyl or a radical corresponding to the formula:

$$—R_{40}—N(R_{38})_2,$$

$R_{40}$ representing a $—CH_2—CH_2—$, $—CH_2—CH_2—CH_2—$ or $—CH_2—CH(CH_3)—$ group, $R_{38}$ having the meanings mentioned above, as well as the higher homologues of these radicals and containing up to 6 carbon atoms.

(8) amphoteric polymers of the type $—D—X—D—X$ chosen from:

a) polymers obtained by the action of chloroacetic acid or sodium chloroacetate on compounds containing at least one unit of formula:

$$—D—X—D—X—D—$$ (XIX)

where D denotes a radical

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula:

$$—D—X—D—X—$$ (XX)

in which D denotes a radical

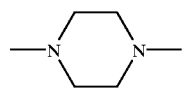

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

Among the cationic or amphoteric substantive polymers which can be used according to the invention, those which are preferred in particular are:

the dimethyidiallylammonium chloride homopolymer sold under the name MERQUAT 100 Dry by the company Calgon;

the copolymers of dimethyldiallylammonium chloride and of acrylamide sold under the name MERQUAT 2200 by the company Calgon;

the polymers of poly(quaternary ammonium) type prepared and described in French patent 2,270,846, the disclosure of which is hereby incorporated by reference, comprising repeating units corresponding to formula (XXI) below:

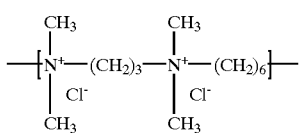
(XXI)

and, in particular, those whose weight-average molar mass, determined by gel permeation chromatography, ranging from 9500 to 9900;

the polymers of poly(quaternary ammonium) type prepared and described in French patent 2,270,846, comprising repeating units corresponding to the formula (XXII) below:

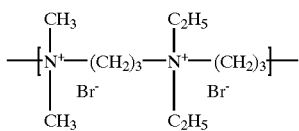
(XXII)

and, in particular, those whose weight-average molar mass, determined by gel permeation chromatography, is about 1200;

the polymers of poly(quaternary ammonium) type described in U.S. Pat. Nos. 4,390,689; 4,702,906 and 4,719,282, the disclosures of which are hereby incorporated by reference, and comprising repeating units corresponding to formula (XXIII) below:

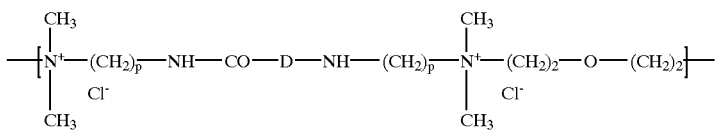
(XXIII)

in which
p is an integer ranging from 1 to 6,
D represents a single bond or a group —(CH$_2$)$_r$—CO— in which r is 4 or 7, and, in particular, those whose weight-average molar mass is less than 100,000, preferably less than or equal to 50,000;

the following amphoteric copolymers:

the diallyldimethylammonium chloride/acrylic acid (80/20) copolymer sold under the name MERQUAT 280 Dry by the company Calgon (CTFA name: Polyquaternium-22);

the dimethyldiallylammonium chloride/acrylic acid (95/5) copolymer sold under the name MERQUAT 295 Dry by the company Calgon (CTFA name: Polyquaternium-22);

the copolymer of methacrylamidopropyltrimonium chloride, of acrylic acid and or methyl acrylate, sold under the name MERQUAT 2001 by the company Calgon (CTFA name: Polyquaternium47); and the acrylamide/dimethyldiallylammonium chloride/acrylic acid terpolymer sold under the name MERQUAT Plus 3330 Dry by the company Calgon (CTFA name: Polyquaternium-39).

In the above list of substantive polymers, the amphoteric copolymers Polyquaternium-22, Polyquaternium-39 and Polyquaternium47 (CTFA names) are preferred most particularly.

The amounts of cationic or amphoteric substantive polymers in the compositions according to the present invention are generally from 0.03 to 30% by weight relative to the total weight of the composition.

The water-soluble thickening polymers which can be used according to the present invention encompass all the synthetic water-soluble polymers or those of natural origin which are conventionally used in cosmetics. Examples of synthetic thickening polymers include, for example, are polyvinylpyrrolidone, polyacrylic acid, polyacrylamide, polyacrylamidomethylpropanesulphonic acid or copolymers thereof, these polymers being crosslinked or non crosslinked. The thickening polymers of natural origin which can be used according to the present invention are polymers comprising at least one sugar unit, namely:

(a) nonionic guar gums;
(b) biopolysaccharide gums of microbial origin such as scleroglucan gum and xanthan gum;
(c) gums derived from plant exudates such as gum arabic, ghatti gum, karaya gum or gum tragacanth;
(d) gums extracted from algae, such as carrageenans or agar;
(e) gums obtained from plant extracts, such as carob gum or pectins extracted from fruit pulp;
(f) alginates;
(g) starches; and
(h) hydroxyalkylcelluloses and carboxyalkylcelluloses.

In the present invention, the expression "sugar unit" means a monosaccharide moiety or an oligo- or polysaccharide moiety comprising the same type of saccharide units (oligo- or polyholosides) or of several types of different saccharide units (oligo- or polyheterosides). The saccharide units of all these polymers can bear one or more substituents, for example alkyl, hydroxyalkyl, alkoxy, acyloxy or carboxyl groups, the alkyl radicals comprising from 1 to 4 carbon atoms. The nonionic guar gums can be modified or unmodified. The unmodified guar gums are, for example, products sold under the name VIDOGUM GH 175 by the company Unipectine and under the name JAGUAR C by the company Mayhall.

According to the present invention, it is also possible to use nonionic guar gums modified with $C_1$–$C_4$ hydroxyalkyl groups, for example hydroxymethyl, hydroxyethyl, hydroxypropyl and hydroxybutyl groups. These modified guar gums are well known in the art and can be prepared by reacting guar gum with suitable alkylene oxides. The degree of hydroxyalkylation (ratio of the number of alkylene oxide molecules fixed to the initial number of free hydroxyl groups) preferably ranges from 0.4 to 1.2. Such modified nonionic guar gums are sold, for example, under the names JAGUAR HP8, JAGUAR HP60, JAGUAR HP120, JAGUAR DC293 and JAGUAR HP105 by the company Rhône-Poulenc (Mayhall) or under the name GALACTASOL 4H4FD2 by the company Aqualon.

The biopolysaccharide gums of microbial origin, such as scleroglucan gum or xanthan gum, the gums obtained from plant exudates, such as gum arabic, ghatti gum, karaya gum or gum tragacanth, the algal extracts, such as carrageenans or agar, the plant extracts, such as carob gum or pectins, the alginates, the starches and the hydroxyalkylcelluloses and carboxyalkylcelluloses are well known in the art and are described in particular in the "Handbook of Water Soluble Gums and Resins" by Robert L. Davidson, published by McGraw Hill Book Company (1980). Among these gums, the scleroglucans are represented by the products sold by the company Sanofi Bio Industries under the name ACTIGUM CS, and in particular under the name ACTIGUM CS 11, and by the company Alban Muller International under the name AMIGEL. It is also possible to use other scleroglucans, for example, a scleroglucan treated with glyoxal described in patent application FR-A-2,633,940, the disclosure of which is hereby incorporated by reference.

The xanthan gums which can be used as thickeners in the compositions of the present invention are represented, for example, by the products sold under the names KELTROL, KELTROL T, KELTROL TF, KELTROL BT, KELTROL RD and KELTROL CG by the company Nutrasweet Kelco, or under the names RHODICARE S or RHODICARE H by the company Rhodia Chimie.

The hydroxyalkylcelluloses are generally hydroxy($C_1$–$C_4$ alkyl)celluloses and, more particularly, hydroxyethylcelluloses. They are available, for example, under the names CELLOSIZE QP3L, CELLOSIZE QP4400H, CELLOSIZE QP30000H, CELLOSIZE HEC30000A or CELLOSIZE POLYMER PCG10 by the company Amerchol, under the names NATROSOL 250HHR, NATROSOL 250MR, NATROSOL 250M, NATROSOL 250HHXR, NATROSOL 250HHX, NATROSOL 250HR or NATROSOL HX by the company Hercules or under the name TYLOSE H1000 by the company Hoechst. The hydroxyalkylcelluloses can also be hydroxypropylcelluloses sold under the names KLUCEL EF, KLUCEL H, KLUCEL LHF, KLUCEL MF or KLUCEL G by the company Aqualon.

Among the carboxyalkylcelluloses which are preferably used is the carboxymethylcellulose which is sold, for example, under the names BLANOSE 7M8/SF, BLANOSE RAFFINÉE 7M, BLANOSE 7LF, BLANOSE 7MF, BLANOSE 9M31F, BLANOSE 12M31XP, BLANOSE 12M31P, BLANOSE 9M31XF, BLANOSE 7H, BLANOSE 7M31 or BLANOSE 7H3SXF by the company Aqualon, under the names AQUASORB A500 and AMBERGUM 1221 by the company Hercules, under the names CELLOGEN HP810A and CELLOGEN HP6HS9 by the company Montello or under the name PRIMELLOSE by the company Avebe.

The water-soluble thickening polymers which can be used particularly preferably as conventional thickeners in the anhydrous bleaching composition of the present invention are guar gums, guar gum derivatives or hydroxyalkylcelluloses.

The water-soluble thickener(s) described above is(are) generally used in a proportion of from 0.03 to 30% by weight, preferably a proportion of from 0.3 to 15% by weight, relative to the anhydrous composition.

A subject of the present invention is also a process for bleaching keratin fibers, in particular, human hair.

This process comprises
  preparing the ready-to-use composition described above,
  applying the composition to the region of keratin fibers to be bleached,
  leaving the mixture to stand on the fibers for a period sufficient to obtain the desired bleaching, this period generally ranging from 10 minutes to one hour, preferably from 10 to 45 minutes, and removing the bleaching mixture by rinsing with water, followed by washing with a shampoo, and then drying.

Another subject of the invention is a packaging device in several parts, also known as a packaging "kit," comprising at least three compartments, the first of which contains a peroxygenated salt as defined above, the second of which contains a water-soluble solvent as defined above and the alkaline agent, and the third of which contains an aqueous hydrogen peroxide composition, the nonionic and/or anionic amphiphilic polymer(s) comprising at least one fatty chain being introduced into one or more of these compartments.

The present invention is further illustrated by the following examples, which are merely illustrative of the invention and should not be construed as limiting the invention as claimed.

EXAMPLE 1

The following compositions A and B were prepared:

| Composition A | |
|---|---|
| Decyl alcohol ethoxylated with 3 mol of EO | 30 g |
| Decyl alcohol ethoxylated with 5 mol of EO | 26 g |
| Oleic acid | 10 g |
| Oleic alcohol | 3 g |
| Propylene glycol | 9 g |
| Oleocetyl alcohol ethoxylated with 30 mol of EO | 4.5 g |
| Ethylene glycol monobutyl ether | 3 g |
| Aqueous ammonia containing 20.5% $NH_3$ | 9 g |
| Water | q.s. 100 g |
| Composition B | |
| Sodium persulphate | 26 g |
| Potassium persulphate | 40 g |
| Sodium metasilicate | 14 g |
| Ammonium chloride | 5 g |
| EDTA | 1 g |
| Sodium lauryl sulphate | 2 g |
| Cetylhydroxyethylcellulose | 2 g |
| Silica | q.s. 100 g |

60 g of composition A, 20 g of composition B and 100 g of aqueous hydrogen peroxide solution at 6% by weight were mixed together.

The viscosity of the mixture varied very little over time and the mixture had good bleaching power.

EXAMPLE 2

The bleaching composition below was prepared (amounts in % by weight):

| Lauareth-5 carboxylic acid | 4 |
|---|---|
| Ethanolamine | 0.6 |
| Deceth-3 | 4 |
| Deceth-5 | 1.5 |
| PPG myristyl ether | 2 |
| Oleth-10 | 1.5 |
| Oleyl alcohol | 1.5 |
| Ethanol | 5 |
| Methoxyisopropanol | 6.5 |
| Polyglyceryl-4 oleyl ether | 2 |
| Merquat 100 | 1.5 |
| Serad FX 1100 | 1 |
| Hydrogen peroxide | 3 |
| Sequestering agent | 0.2 |
| Fragrance | 1 |
| Water | q.s. 100 g |

This composition, intended to be applied immediately to hair to be bleached, was applied for 45 minutes under a hood.

After rinsing and drying, a uniform bleaching effect was obtained.

The foregoing written description relates to various embodiments of the present invention. Numerous changes and modifications may be made therein without departing from the spirit and scope of the invention as defined in the following claims.

What is claimed is:

1. A ready-to-use aqueous composition for bleaching keratin fibers, comprising:
   at least one alkaline agent,
   from 2 to 20% by weight of at least one peroxygenated salt, relative to the total weight composition
   hydrogen peroxide,
   at least one water-soluble solvent, and
   at least one amphiphilic polymer chosen from nonionic and anionic amphiphilic polymers and comprising at least one fatty chain.

2. A composition according to claim 1, wherein said composition is in a medium suitable for bleaching.

3. A composition according to claim 1, wherein said keratin fibers are human keratin fibers.

4. A composition according to claim 1, wherein said at least one nonionic amphiphilic polymer comprising at least one fatty chain is chosen from
   celluloses or hydroxyalkylcelluloses modified with polyalkoxylated alkylphenol groups or with groups comprising at least one fatty chain chosen from alkyl, arylalkyl and alkylaryl fatty chains containing a $C_8$–$C_{22}$ alkyl group;
   hydroxypropyl guars modified with groups comprising at least one $C_8$–$C_{22}$ fatty chain;
   polyurethanes comprising at least one fatty chain of $C_8$–$C_{30}$ alkyl or alkenyl type;
   copolymers of vinylpyrrolidone and of hydrophobic monomers containing a fatty chain;
   copolymers of $C_1$–$C_6$ alkyl (meth)acrylates and of amphiphilic monomers comprising at least one fatty chain;
   copolymers of hydrophilic (meth)acrylates and of hydrophobic monomers comprising at least one fatty chain.

5. A composition according to claim 1, wherein said at least one nonionic amphiphilic polymer is a hydroxyethylcellulose modified with groups comprising at least one $C_8$–$C_{22}$ alkyl radical or a polyurethane comprising at least one $C_{10}$–$C_{20}$ alkyl chain.

6. A composition according to claim 1, wherein said at least one anionic amphiphilic polymer comprising at least one fatty chain is a copolymer comprising
   hydrophilic units derived from at least one monomer containing ethylenic unsaturation and bearing a carboxylic acid function, and
   hydrophobic units derived from at least one monomer containing ethylenic unsaturation and bearing a hydrophobic side chain.

7. A composition according to claim 6, wherein said at least one monomer containing ethylenic unsaturation and bearing a carboxylic acid function is chosen from ethacrylic acid, methacrylic acid and acrylic acid.

8. A composition according to claim 7, wherein said at least one monomer containing ethylenic unsaturation and bearing a carboxylic acid function is chosen from methacrylic acid and acrylic acid.

9. A composition according to claim 6, wherein said monomer containing ethylenic unsaturation and bearing a hydrophobic side chain is chosen from $C_{10}$–$C_{30}$ alkyl ethacrylates, methacrylates and/acrylates.

10. A composition according to claim 9, wherein said monomer containing ethylenic unsaturation and bearing a hydrophobic side chain is chosen from $C_{12}$–$C_{22}$ alkyl ethacrylates.

11. A composition according to claim 6, wherein said monomer containing ethylenic unsaturation and bearing a hydrophobic side chain is chosen from allyl fatty alkyl ethers corresponding to the formula $$CH_2=CR'CH_2-O-B_n-R \qquad (I)$$

in which
   R' is chosen from a hydrogen atom and a methyl group,
   B is an ethylenoxy group,
   n is an integer ranging from 0 to 100,
   R is a hydrocarbon-based group chosen from alkyl, arylalkyl, aryl, alkylaryl and cycloalkyl residues comprising from 8 to 30 carbon atoms.

12. A composition according to claim 11, wherein said R is a hydrocarbon-based group chosen from alkyl, arylalkyl, aryl, alkylaryl and cycloalkyl residues comprising from 10 to 24 carbon atoms.

13. A composition according to claim 6, wherein said at least one anionic amphiphilic polymer comprising at least one fatty chain further comprises units derived from a crosslinking monomer containing two non-conjugated ethylenic double bonds.

14. A composition according to claim 13, wherein said crosslinking monomer is chosen from diallyl phthalate, allyl (meth)acrylate, divinylbenzene, (poly)ethylene glycol dimethacrylate, methylenebisacrylamide, polyallylsucrose and poly-allylpentaerythritol.

15. A composition according to claim 6, wherein said at least one anionic amphiphilic polymer comprising at least one fatty chain is a crosslinked copolymer of acrylic acid and of $C_{10-30}$ alkyl acrylate.

16. A composition according to claim 1, wherein said at least one amphiphilic polymer is present in said composition in an amount ranging from 0.01 to 10% by weight, relative to the total weight of the composition.

17. A composition according to claim 16, wherein said at least one amphiphilic polymer is present in said composition in an amount ranging from 0.1 to 5% by weight, relative to the total weight of the composition.

18. A composition according to claim 1, wherein said at least one water-soluble solvent is chosen from linear or branched $C_{16}$ aliphatic monoalcohols, linear or branched $C_{3-20}$ aliphatic polyols, and polyol ethers.

19. A composition according to claim 18, wherein said polyol ethers are chosen from $C_{1-6}$ aliphatic mono- or diethers of $C_{2-9}$ polyols and $C_{6-9}$ aromatic ethers of $C_{2-9}$ polyols.

20. A composition according to claim 1, wherein said at least one water-soluble solvent is present in said composition in an amount ranging from 0.1 to 10% by weight relative to the total weight of the composition.

21. A composition according to claim 20, wherein said at least one water-soluble solvent is present in said composition in an amount ranging from 0.5 to 8% by weight relative to the total weight of the composition.

22. A composition according to claim 1, wherein said at least one alkaline agent is chosen from aqueous ammonia and organic amines.

23. A composition according to claim 22, wherein said at least one alkaline agent is chosen from monoethanolamine, diethanolamine, triethanolamine, 2-amino-2-methyl-1-propanol, diaminopropane, hydroxyalkylamines and ethylenediamines which are oxyethylenated and/or oxypropylenated.

24. A composition according to claim 1, wherein said at least one peroxygenated salt is chosen from ammonium and alkali metal persulphates, percarbonates and perborates.

25. A composition according to claim 24, wherein said at least one peroxygenated salt is chosen from sodium persulphate and potassium persulphate.

26. A composition according to claim 1, wherein said at least one peroxygenated salt is present in said composition in an amount ranging from 4 to 15% by weight relative to the total weight of the composition.

27. A composition according to claim 1, wherein said hydrogen peroxide is present in said composition in an amount ranging from 0.5 to 10% by weight, relative to the total weight of the composition.

28. A composition according to claim 27, wherein said hydrogen peroxide is present in said composition in an amount ranging from 1 to 8% by weight, relative to the total weight of the composition.

29. A composition according to claim 1, further comprising bleaching adjuvants chosen from agents for controlling the release of oxygen, anionic, nonionic, cationic, amphoteric or zwitterionic surfactants and mixtures thereof, mineral or plant oils, waxes, binders, mineral fillers, opacifiers, sequestering agents, fragrances and polymers.

30. A composition according to claim 29, further comprising at least one polymer chosen from natural and synthetic water-soluble thickening polymers.

31. A composition according to claim 30, wherein said at least one polymer chosen from natural and synthetic water-soluble thickening polymers is present in said composition in an amount ranging from 0.03 to 30% by weight, relative to the total weight of the composition.

32. A composition according to claim 31, wherein said at least one polymer chosen from natural and synthetic water-soluble thickening polymers is present in said composition in an amount ranging from 0.3 to 15% by weight, relative to the total weight of the composition.

33. A composition according to claim 29, further comprising at least one polymer chosen from cationic and amphoteric substantive polymers.

34. A composition according to claim 33, wherein said at least one polymer chosen from cationic and amphoteric substantive polymers is present in said composition in an amount ranging from 0.03 to 30% by weight, relative to the total weight of the composition.

35. A composition according to claim 29, wherein said composition comprises from 0.01 to 40% by weight of at least one surfactant, relative to the total weight of the composition.

36. A composition according to claim 35, wherein said at least one surfactant is present in said composition in an amount ranging from 0.1 to 30% by weight, relative to the total weight of the composition.

37. A process for bleaching keratin fibers, comprising preparing, immediately before application, an aqueous bleaching composition, wherein said composition comprises at least one alkaline agent, from 2 to 20% by weight of at least one peroxygenated salt, hydrogen peroxide, at least one water-soluble solvent, and at least one amphiphilic polymer chosen from nonionic and anionic amphiphilic polymers and comprising at least one fatty chain;

applying said composition to the keratin fibers to be bleached;

leaving the mixture to stand on the fibers for a period sufficient to obtain the desired bleaching effect; and removing the bleaching mixture by rinsing with water, followed by washing with a shampoo, and then drying.

38. A process according to claim 37, wherein said keratin fibers are human hair.

39. A multi-compartment device for bleaching keratin fibers, comprising at least three compartments, wherein a first compartment comprises a peroxygenated salt chosen from ammonium and alkali metal persulphates, percarbonates and perborates;

a second compartment comprises:
  a water-soluble solvent chosen from linear or branched $C_{1-6}$ aliphatic monoalcohols, linear or branched $C_{3-20}$ aliphatic polyols, and polyol ethers, and
  an alkaline agent chosen from aqueous ammonia and organic amines; and a third compartment comprises an aqueous hydrogen peroxide composition, and wherein at least one amphiphilic polymer chosen from nonionic and anionic amphiphilic polymers and comprising at least one fatty chain is present in any of said at least three compartments.

40. A multi-compartment device according to claim 39, wherein said said polyol ethers are chosen from $C_{1-6}$ aliphatic mono- or diethers of $C_{2-9}$ polyols and $C_{6-9}$ aromatic ethers of $C_{2-9}$ polyols.

41. A multi-compartment device according to claim 39, wherein said keratin fibers are human keratin fibers.

42. A multi-compartment device according to claim 41, wherein said human keratin fibers are human hair.

* * * * *

UNITED STATES PATENT AND TRADEMARK OFFICE
CERTIFICATE OF CORRECTION

PATENT NO.     : 6,641,618 B1
DATED          : November 4, 2003
INVENTOR(S)    : Legrand et al.

It is certified that error appears in the above-identified patent and that said Letters Patent is hereby corrected as shown below:

Column 21,
Line 9, "composition for bleaching" should read -- bleaching composition for --.
Line 13, "weight composition" should read -- weight of the composition --.
Line 19, "chain." should read
    -- chain,
    wherein said at least one alkaline agent, said at least one peroxygenated salt, said hydrogen peroxide, said at least one water-soluble solvent and said at least one amphiphilic polymer are present in a combined amount effective to bleach keratin fibers. --.

Column 22,
Line 2, "and/acrylates." should read -- and acrylates. --.
Line 49, "$C_{16}$" should read -- $C_{1-6}$ --.

Column 24,
Line 14, "chain;" should read
    -- chain,
    wherein said at least one alkaline agent, said at least one peroxygenated salt, said hydrogen peroxide, said at least one water-soluble solvent and said at least one amphiphilic polymer are present in a combined amount effective to bleach keratin fibers; --.
Line 24, "device for bleaching" should read -- bleaching device for --.
Line 37, "composition, and wherein" should read
    -- composition, wherein --.

UNITED STATES PATENT AND TRADEMARK OFFICE
CERTIFICATE OF CORRECTION

PATENT NO. : 6,641,618 B1
DATED : November 4, 2003
INVENTOR(S) : Legrand et al.

It is certified that error appears in the above-identified patent and that said Letters Patent is hereby corrected as shown below:

Column 24, cont'd,
Lines 40-41, "compartments." should read
 -- compartments, and
 wherein said at least one alkaline agent, said at least one peroxygenated salt, said hydrogen peroxide, said at least one water-soluble solvent and said at least one amphiphilic polymer are present in a combined amount effective to bleach keratin fibers. --.

Signed and Sealed this

Twenty-third Day of March, 2004

JON W. DUDAS
*Acting Director of the United States Patent and Trademark Office*